(12) United States Patent
Priem et al.

(10) Patent No.: US 12,329,503 B2
(45) Date of Patent: Jun. 17, 2025

(54) METHOD AND SYSTEM FOR EVALUATING THE QUALITY OF RATIO OF RATIOS VALUES

(71) Applicant: BIOSENCY, Saint-Grégoire (FR)

(72) Inventors: Gurvan Priem, Rennes (FR); Quentin Bodinier, Lyons (FR)

(73) Assignee: BIOSENCY, Saint-Grégoire (FR)

(*) Notice: Subject to any disclaimer, the term of this patent is extended or adjusted under 35 U.S.C. 154(b) by 679 days.

(21) Appl. No.: 17/764,311

(22) PCT Filed: Oct. 2, 2020

(86) PCT No.: PCT/EP2020/077727
§ 371 (c)(1),
(2) Date: Mar. 28, 2022

(87) PCT Pub. No.: WO2021/064212
PCT Pub. Date: Apr. 8, 2021

(65) Prior Publication Data
US 2022/0369943 A1    Nov. 24, 2022

(30) Foreign Application Priority Data
Oct. 2, 2019    (EP) ................. 19306266

(51) Int. Cl.
*A61B 5/024*    (2006.01)
*A61B 5/00*    (2006.01)
*A61B 5/1455*    (2006.01)

(52) U.S. Cl.
CPC ...... *A61B 5/02416* (2013.01); *A61B 5/14551* (2013.01); *A61B 5/72* (2013.01); *A61B 5/681* (2013.01)

(58) Field of Classification Search
CPC . A61B 5/7221; A61B 5/0205; A61B 5/14551; A61B 5/681; A61B 5/721; A61B 5/7253; A61B 5/02416; A61B 2562/0219
See application file for complete search history.

(56) References Cited

U.S. PATENT DOCUMENTS

| | | |
|---|---|---|
| 2014/0031652 A1 | 1/2014 | Baker, Jr. |
| 2016/0354017 A1 | 12/2016 | Meehan et al. |

(Continued)

FOREIGN PATENT DOCUMENTS

| | | |
|---|---|---|
| EP | 3491999 A2 | 6/2019 |
| WO | 2017001955 A1 | 1/2017 |

OTHER PUBLICATIONS

Schramm et al., "Effect of local limb temperature on pulse oximetry and the plethysmographic pulse wave"; International Journal of Clinical Monitoring and Computing; 1997; pp. 17-22.

(Continued)

*Primary Examiner* — Eric F Winakur
(74) *Attorney, Agent, or Firm* — Maier & Maier, PLLC (57) ABSTRACT

A method intended for the evaluation of the quality of ratio of ratios (RR) values computed for at least two photoplethysmographic (PPG) signals corresponding to distinct wavelengths, each PPG signal including successive heartbeat patterns. The method includes the steps of: segmenting the PPG signals into a plurality of signal segments each corresponding to one heartbeat pattern; for each given signal segment, computing a sequence of RR values; and evaluating, for each given signal segment, a quality index of the sequence of computed RR values on the basis of a computed heart rate and/or a measured peripheral temperature corresponding to the given signal segment.

14 Claims, 5 Drawing Sheets

(56) References Cited

U.S. PATENT DOCUMENTS

2016/0360984 A1* 12/2016 Albadawi .......... A61B 5/14551
2018/0325457 A1    11/2018 Ghosh et al.

OTHER PUBLICATIONS

International Search Report and Written Opinion issued on Nov. 20, 2020 in corresponding International Patent Application No. PCT/EP2020/077727; 14 pages.

* cited by examiner

METHOD AND SYSTEM FOR EVALUATING THE QUALITY OF RATIO OF RATIOS VALUES

FIELD

The present invention relates to a method and a system for evaluating the quality of ratio of ratios (RR) values computed for at least two photoplethysmographic (PPG) signals corresponding to distinct wavelengths. The invention is advantageous for the determination of blood oxygen saturation (SpO2) with ambulatory measurement devices, as it allows to discriminate, for the computation of ratio of ratios (RR) values, between acquisitions that are exploitable and those that are to be rejected, for example due to motion artifacts, noisy environments, or unsuitable values of parameters influencing the physiological signal, in particular low peripheral perfusion.

BACKGROUND

The assessment of oxygen saturation in arterial blood by pulse oximetry (SpO2) is based on the different light absorption spectra for oxygenated and deoxygenated hemoglobin and the analysis of photoplethysmographic (PPG) signals acquired at two distinct wavelengths. More specifically, PPG curves in two wavelengths $\lambda_1$ and $\lambda_2$ are recorded and SpO2 is derived from the ratio of ratios RR which is defined by:

$$RR = \frac{\left(\frac{AC}{DC}\right)_{\lambda_1}}{\left(\frac{AC}{DC}\right)_{\lambda_2}}$$

where AC is the peak-to-peak amplitude of the PPG pulse and DC is the baseline of the PPG pulse. Then, it can be shown that $SpO_2 = f(RR)$ where $f$ is a rational function which can be approximated by a polynomial function.

One difficult task in the design of $SpO_2$ sensors is the calibration of the function $f$. This is usually performed thanks to a calibration study in which healthy subjects undergo a controlled hypoxia protocol which follows specific standards, this protocol being implemented while the subject is wearing both the device under test and reference devices the performance of which has already been certified. Then, the calibration is performed by finding the coefficients $\alpha_d$ that solve the following optimization problem:

$$\min_{\alpha_d} \sqrt{\frac{1}{N}\sum_{n=0}^{N-1}\left(\left(\sum_{d=0}^{D-1}\alpha_d RR_n^d\right) - SpO_{2_n}^{ref}\right)^2},$$

$$s.t.\ \alpha_d \in \mathbb{R}\ \forall\ d \in 0\ ...\ D-1$$

i.e. by finding the polynomial function which minimizes the root mean square error between N reference points $SpO_{2_n}^{ref}$ and the corresponding estimated values obtained based on the measurement of $RR_n$. In this respect, a second order polynomial calibration model is classically used, which takes into account the values of RR and $RR^2$.

However, reflectance pulse oximetry in ambulatory setups, e.g. at the wrist, is much more complex than transmittance pulse oximetry at the finger under human supervision, as is most common. In particular, the ratio of light passing through the blood vessels in a reflectance setup is much lower than that observed in a transmittance setup. Then, the AC signal is highly attenuated and the AC-to-DC ratio, also called the "perfusion index", is much lower. In addition to low perfusion index, in ambulatory setups, it is required to cope with motion artifacts, while also ensuring an assessment of the quality of each measurement in an automatic and unsupervised manner.

It is these drawbacks that the invention is intended more particularly to remedy by proposing a method and a system for evaluating the quality of RR values computed for PPG signals corresponding to distinct wavelengths, which make it possible to automatically reject RR values that are not exploitable, for example due to motion artifacts, noisy environments, or unsuitable values of parameters influencing the physiological signal, in particular low peripheral perfusion, so that the SpO2 of a subject can be determined with improved accuracy even in ambulatory setups.

SUMMARY

For this purpose, a subject of the invention is a method for evaluating the quality of ratio of ratios (RR) values computed for at least two photoplethysmographic (PPG) signals corresponding to distinct wavelengths, wherein each PPG signal comprises successive heartbeat patterns, said method comprising:
  segmenting the PPG signals into a plurality of signal segments each corresponding to one heartbeat pattern;
  for each given signal segment, computing a sequence of RR values;
  evaluating, for each given signal segment, a quality index of the sequence of computed RR values on the basis of a computed heart rate and/or a measured peripheral temperature corresponding to the given signal segment.

The method of the invention provides a specific RR quality assessment stage based on the consistency of the RR values with a computed heart rate and/or based on information from a peripheral temperature sensor. This is particularly interesting in the context of reflectance measurements in an ambulatory setup which are typically correlated with low perfusion and therefore low RR estimation quality.

According to one embodiment, the quality index of a sequence of computed RR values involves a term resulting from a comparison between the number of heartbeats in the period of time on which the computed RR values are determined and the number of heartbeats calculated from the computed heart rate for said period of time.

According to one embodiment, the computed RR values are obtained from a first PPG signal corresponding to a red wavelength and a second PPG signal corresponding to an infrared wavelength, whereas the computed heart rate is obtained by identifying a maximum peak in the frequency domain in a third PPG signal corresponding to a third wavelength, such as a green wavelength. In this embodiment, the RR quality assessment stage is based on the consistency of the RR values with a heart rate measurement obtained thanks to the third wavelength channel. This solution has the advantage of making the exploitation of segmented red and IR signals in a signal quality assessment stage unnecessary. This is particularly interesting as these techniques can be much more complex to implement than simply assessing the consistency of the obtained RR sequence.

According to one embodiment, the method comprises, for the segmentation of the PPG signals into a plurality of signal segments:

extracting the heartbeat patterns from the third PPG signal corresponding to a third wavelength;

segmenting the first and second PPG signals into a plurality of signal segments using the heartbeat patterns extracted from the third PPG signal.

This embodiment corresponds to a specific segmentation strategy of the first and second PPG channels, based on an additional PPG channel corresponding to a third wavelength which is exploited to detect the instants at which heart beats occur. According to one embodiment, the wavelength of the third PPG signal is comprised approximately in the range between 520 nm and 530 nm corresponding to green light PPG signal. This embodiment is particularly advantageous since green light PPG reflects the volume change in blood vessels in the skin surface due to the relatively shallow penetration depth of the green light in tissue, therefore green light PPG allows good quality signal acquisition. As consequence, analysis of green light PPG signal allows to accurately identify the peaks and therefore the heartbeat patterns so as to obtain good quality measurement of heart rate. In another embodiment, the third PPG signal is obtained from a light source which is close to the photodetectors so as to obtain a high signal-to-noise ratio resulting in a satisfying estimation of the heart rate.

According to a specific embodiment, the method comprises:

segmenting a first PPG signal ($x_r$) corresponding to a red wavelength and a second PPG signal ($x_{ir}$) corresponding to an infrared wavelength into a plurality of signal segments each corresponding to one heartbeat, by:

extracting a sequence of heartbeat instants $t_{b,g}[n]$ from a third PPG signal ($x_g$) corresponding to a third wavelength;

segmenting the first and second PPG signals ($x_r$, $x_{ir}$) into a plurality of signal segments ($x_r[n,:]$, $x_{ir}[n,:]$), each signal segment corresponding to one heartbeat, using the sequence of heartbeat instants $t_{b,g}[n]$ extracted from the third PPG signal ($x_g$), for each given signal segment ($x_r[n,:]$, $x_{ir}[n,:]$), computing a sequence of RR values, evaluating, for each given signal segment ($x_r[n,:]$, $x_{ir}[n,:]$), a quality index (q) of the sequence of computed RR values on the basis of a computed heart rate and/or a measured peripheral temperature corresponding to the given signal segment.

According to one embodiment, the quality index of a sequence of computed RR values involves a term resulting from a comparison between the number of heartbeat patterns in the period of time on which the computed RR values are determined and the number of heartbeats calculated from the computed heart rate for said period of time.

According to one embodiment, the computed heart rate is obtained by identifying a maximum peak in the frequency domain in the third PPG signal ($x_g$) corresponding to a third wavelength.

According to one embodiment, the sequence of heartbeat instants $t_{b,g}[n]$ is extracted from the third PPG signal and applied to the first and second PPG signals such that:

$$\forall n, t_{b,r}[n] = t_{b,ir}[n] = t_{b,g}[n]$$

each heartbeat signal segment of the first PPG signal ($x_r$) and the second PPG signal ($x_{ir}$) being defined according to the following expressions:

$$x_r[n,:] = ppg\_r[\tfrac{1}{2}(t_{b,g}[n] + t_{b,g}[n+1]) : \tfrac{1}{2}(t_{b,g}[n+1] + t_{b,g}[n+2])],$$

$$x_{ir}[n,:] = ppg\_ir[\tfrac{1}{2}(t_{b,g}[n] + t_{b,g}[n+1]) : \tfrac{1}{2}(t_{b,g}[n+1] + t_{b,g}[n+2])].$$

According to another embodiment, each heartbeat instant $t_{b,r}[n]$ and $t_{b,ir}[n]$ is determined, respectively for the first and second PPG signals, by searching the local maximum of the PPG signal closest to the corresponding value of $t_{b,g}[n]$.

According to one embodiment, the quality index of a sequence of computed RR values involves a term resulting from a comparison between a measured peripheral temperature and a reference temperature. In this way, information from a peripheral temperature sensor is integrated at the input of the RR quality assessment. This is particularly interesting in the context of wrist-based measurements in an ambulatory setup as low peripheral temperature is typically correlated with low perfusion and therefore low RR estimation quality.

According to one embodiment, the quality index of a sequence of computed RR values involves a term resulting from the calculation of the dispersion of the computed RR values for the different signal segments.

According to one embodiment, the quality index of a sequence of computed RR values is a product of at least two among the terms resulting from the dispersion calculation, the heartbeat comparison and the temperature comparison.

According to one embodiment, the method further comprises steps of:

for each given signal segment, estimating the fitness of the given signal segment for RR estimation and outputting a signal quality index for the given signal segment, for each given signal segment, evaluating the quality of the computed RR value on the basis of the signal quality index for the given signal segment.

Another subject of the invention is a method for evaluating an SpO2 value based on a ratio of ratios (RR) value evaluated according to the method described above, wherein the photoplethysmographic (PPG) signals are obtained by using LEDs as light sources, the SpO2 value being obtained using a calibration model having as parameters the RR value and the LED current of at least one of the LEDs.

According to one embodiment, the calibration model is a second order polynomial calibration model having as parameters:

the RR value and its squared value $RR^2$, the logarithm of the LED current of at least one of the LEDs and its squared value.

Another subject of the invention is a computer program comprising instructions for the implementation of the steps of a method as described above when the program is executed by a computer.

Another subject of the invention is a non-transitory computer readable medium comprising instructions for the implementation of the steps of a method as described above when the instructions are executed by a computer.

Another subject of the invention is a system for evaluating the quality of ratio of ratios (RR) values computed for at least two photoplethysmographic (PPG) signals corresponding to distinct wavelengths, wherein each PPG signal comprises successive heartbeat patterns, said system comprising:

a segmentation module for segmenting the PPG signals into a plurality of signal segments each corresponding to one heartbeat pattern, a computation module for computing, for each given signal segment, a sequence of RR values, an evaluation module for evaluating, for each given signal segment, a quality index of the sequence of computed RR values on the basis of a computed heart rate and/or a measured peripheral temperature corresponding to the given signal segment.

According to one specific embodiment, the system comprises:
- a segmentation module for segmenting a first PPG signal ($x_r$) corresponding to a red wavelength and a second PPG signal ($x_{ir}$) corresponding to an infrared wavelength into a plurality of signal segments each corresponding to one heartbeat pattern,
- a computation module for computing, for each given signal segment ($x_r[n,:]$, $x_{ir}[n,:]$), a sequence of RR values, by:
  - extracting the heartbeat patterns from the third PPG signal ($x_g$) corresponding to a third wavelength;
  - segmenting the first and second PPG signals ($x_r$, $x_{ir}$) into a plurality of signal segments ($x_r[n,:]$, $x_{ir}[n,:]$) using the heartbeat patterns extracted from the third PPG signal ($x_g$),
- an evaluation module for evaluating, for each given signal segment ($x_r[n,:]$, $x_{ir}[n,:]$), a quality index (q) of the sequence of computed RR values on the basis of a computed heart rate and/or a measured peripheral temperature corresponding to the given signal segment.

Another subject of the invention is a system for performing a pulse oximetry comprising:
- at least two light sources configured to emit light at two distinct wavelengths,
- an acquisition module configured to acquire the photoplethysmographic (PPG) signals resulting from the illumination of tissues of a subject by means of said light sources,
- a system as described above for evaluating the quality of ratio of ratios (RR) values computed for the PPG signals corresponding to the two distinct wavelengths.

According to one embodiment, the system for performing a pulse oximetry further comprises a third light source configured to emit at a third wavelength and located at a position facilitating the measurement of heart rate and a peripheral temperature sensor.

BRIEF DESCRIPTION OF THE DRAWINGS

Features and advantages of the invention will become apparent from the following description of two illustrative embodiments of a method and a system according to the invention, intended for the evaluation of the quality of at least one periodic or quasi-periodic physiological signal, this description being given merely by way of example and with reference to the appended drawings in which.

DETAILED DESCRIPTION

Figure 1:
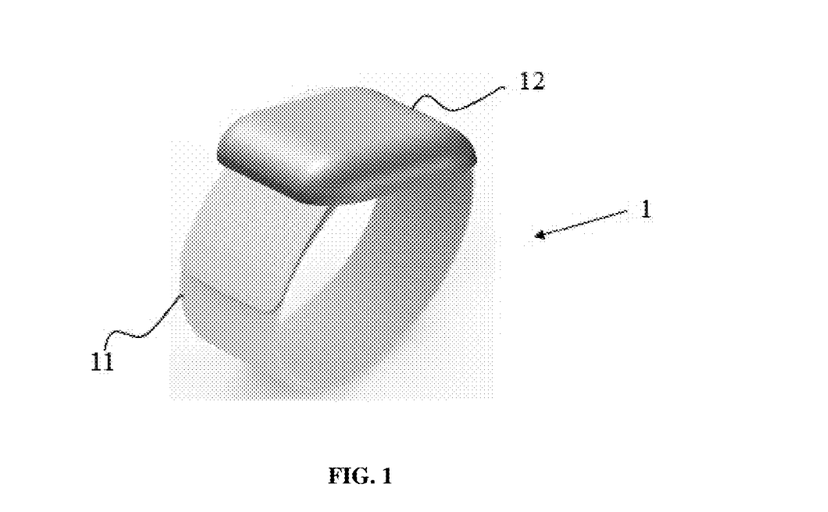
FIG. 1 is a perspective view of a wrist-worn portable monitoring device according to one embodiment of the invention.
Figure 2:
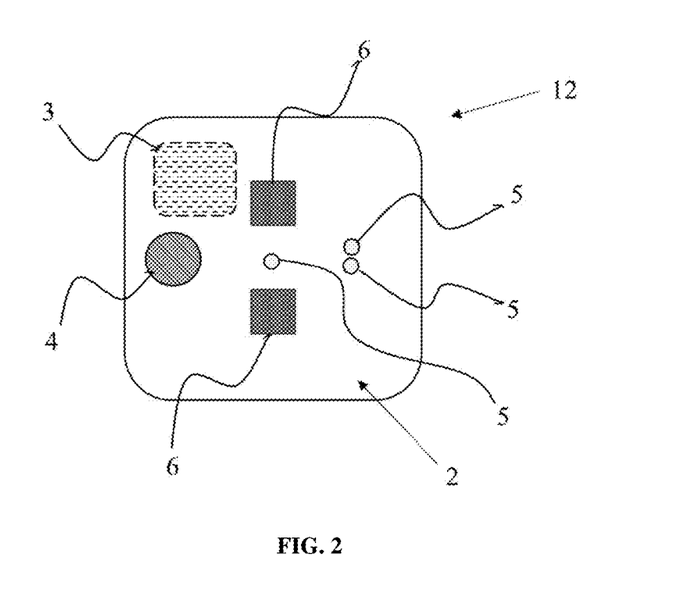
FIG. 2 is a view of the skin-side of the casing of the wrist-worn monitoring device of FIG. 1.

An example of a wrist-worn portable biometric monitoring device 1 is shown in FIGS. 1 and 2. The monitoring device 1 comprises an attachment band 11 and a casing 12 fixed to the attachment band 11. The monitoring device 1 also comprises several active elements housed inside the casing 12, i.e. a PPG sensor 2 (or photoplethysmograph), an inertial motion unit (IMU) 3 and a temperature sensor 4. The attachment band 11 is advantageously flexible and/or compliant so as to conform to the shape of a wrist of a subject. In this way, when the attachment band 11 is in place around a wrist of a subject, the casing 12 and its active elements 2, 3, 4 are close to the skin of the subject, i.e. with little to no gap between the skin-side of the casing 12 and the adjacent surface of the skin of the subject.

Figure 3:
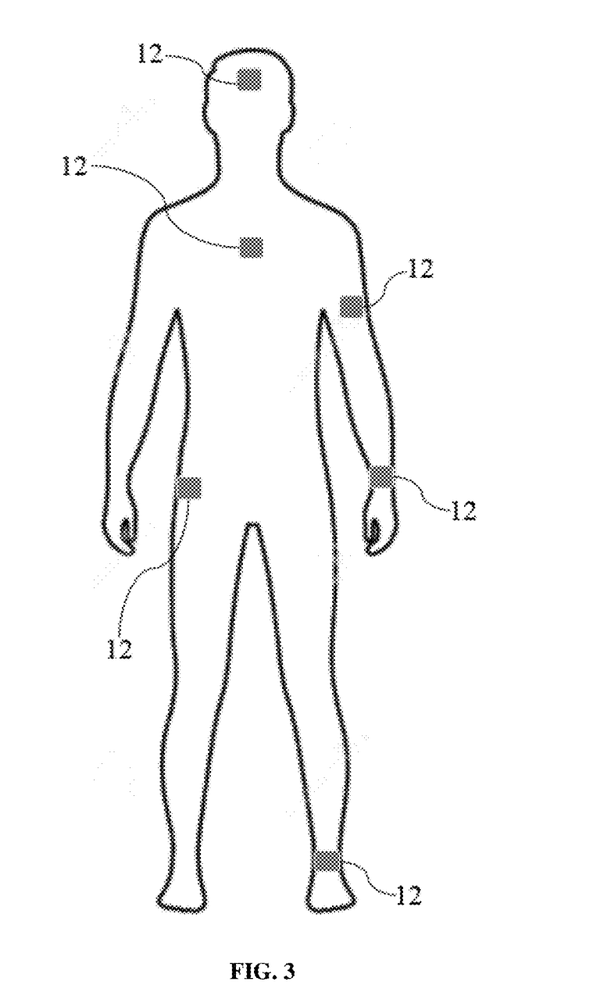
FIG. 3 is a schematic view of possible locations of a casing of a monitoring device according to the invention on the body of a subject.

The attachment band 11 may have an adjustable circumference, therefore allowing it to be closely fitted to the wrist of the subject. The attachment band 11 may be detachable from the casing 12 and, if necessary, replaceable. As illustrated in FIG. 3, the casing 12 may also be associated to attachment bands 11 of various shapes and dimensions, so that it can be worn by a subject in different locations, e.g. on the wrist, the arm, the chest, the forehead, the ankle, the leg, the hip of the subject. In FIG. 3, for clarity purposes, the various attachment bands 11 associated to the casings 12 in the different locations have not been represented.

The PPG sensor 2 of the monitoring device 1 comprises at least two light sources 5 (LED, laser, etc.) and at least one photodetector 6 (photodiode, phototransistor, etc.) arranged relative to one another so that each photodetector 6 receives the light emitted by the light sources 5 after interaction with the tissues of a subject wearing the monitoring device 1. The light sources 5 and the photodetector(s) 6 may be placed on a flexible PCB. The monitoring device 1 also comprises a circuitry configured to determine physiological data of the subject based on the measurements of each photodetector 6, i.e. PPG signals resulting from the emission of the light sources 5, possibly combined with other measurements e.g. from the inertial motion unit 3 and the temperature sensor 4. Examples of physiological data of the subject that can be determined by means of the monitoring device 1 include the heart rate, the respiratory rate and/or the blood oxygen saturation (SpO2) of the subject.

More specifically, in the illustrative embodiment shown in FIG. 2, the PPG sensor 2 includes three light sources 5 which are three LEDs emitting light at, respectively, a red wavelength, an infrared wavelength, and a green wavelength. The PPG sensor 2 also includes two photodetectors 6 placed on both sides of the green LED, whereas the red and infrared LEDs are offset laterally relative to the interspace between the two photodetectors 6. Green light PPG reflects the volume change in blood vessels in the skin surface due to the relatively shallow penetration depth of the green light in tissue. The positioning of the green LED in proximity of the photodetectors 6 is particularly advantageous for the measurement of heart rate since the close distance between the green light LED and the photodetectors contributes to the collection of light reflected at shallow penetration depth in the tissue. Light pipes may be used to optically connect the LEDs 5 and the photodetectors 6 with the surface of the skin of the subject. Beneath the skin, the light from the LEDs 5 scatters off of blood in the body, some of which may be scattered or reflected back into the photodetectors 6. Due to the different positions of the three LEDs 5 in the casing 12 and the different depths of penetration of light into the tissues of the subject for the three wavelengths, different optical paths are obtained for the light of the three LEDs 5, resulting in multiple measurements by the two photodetectors 6. Such multiple measurements ensure a robust evaluation of the physiological data of the subject such as the heart rate, the respiratory rate and/or the SpO$_2$ of the subject.

In this illustrative embodiment, the inertial motion unit 3 is a 6-axis unit comprising a 3-axis gyroscope and a 3-axis accelerometer. Advantageously, the inertial motion unit 3 is entirely housed inside the casing 12, without emerging on the skin-side of the casing 12. This is represented by the dotted lines around the inertial motion unit 3 in FIG. 2, which shows the skin-side of the casing 12. The temperature sensor 4 is configured to monitor the skin temperature of the subject in the vicinity of the PPG sensor. The monitoring of the skin temperature is important because low peripheral temperature is typically correlated with low perfusion and therefore low RR estimation quality. In addition, skin temperature may affect the temperature of the LEDs 5 and thus their emitted wavelength.

The successive steps of a method according to the invention are detailed below with reference to FIG. 4. The method allows the determination of the blood oxygen saturation (SpO2) of a subject, e.g. by means of the portable monitoring device 1 described previously, with improved accuracy.

On each of the red and IR PPG channels of the wrist-worn monitoring device 1, the pulsatile AC signal is obtained thanks to a Butterworth or Chebyschev filter of order comprised between 2 and 4, with cutoff frequencies of 0.5 Hz and 4 Hz. The DC signal is obtained using a low-pass filter having a cutoff frequency of 0.5 Hz.

Figure 5:
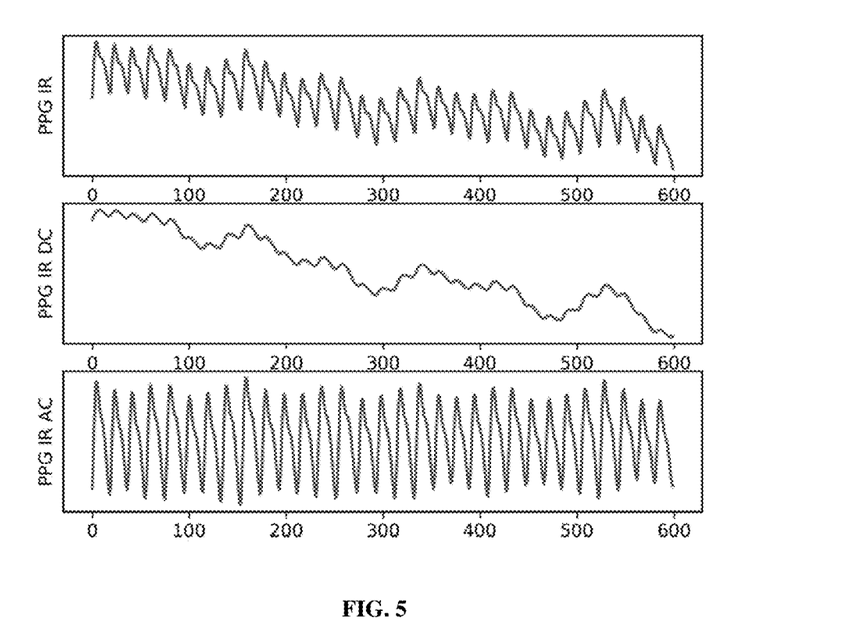
FIG. 5 is a graph showing the AC and DC components of a PPG signal corresponding to the IR channel of the wrist-worn monitoring device of FIG. 1.

By way of example, preprocessed AC and DC components of the PPG signal corresponding to the IR channel of the pulse oximeter are shown in FIG. 5.

In an advantageous manner, information gathered on the green PPG channel of the monitoring device 1 is used to segment the PPG signals from the red and infrared PPG channels. More specifically, a sequence of heartbeat instant $t_{b,g}[n]$ is detected on the green PPG channel and applied on the red and IR PPG channels such that:

$$\forall n, t_{b,r}[n] = t_{b,ir}[n] = t_{b,g}[n].$$

Then, each heartbeat signal segment is constructed on the red and IR PPG channels according to the following expressions:

$$x_r[n,:] = ppg\_r[\tfrac{1}{2}(t_{b,g}[n] + t_{b,g}[n+1]):\tfrac{1}{2}(t_{b,g}[n+1] + t_{b,g}[n+2])],$$

$$x_{ir}[n,:] = ppg\_ir[\tfrac{1}{2}(t_{b,g}[n] + t_{b,g}[n+1]):\tfrac{1}{2}(t_{b,g}[n+1] + t_{b,g}[n+2])].$$

For heartbeat signal segment or heartbeat instant signal segment (also called heartbeat pattern) it has to be understood the segment of signal comprising only one complete pulsation of the heart.

It is noted that, depending on the physical distribution of the LEDs of the pulse oximeter, it is possible that the green optical path differs from the red and IR optical paths. Therefore, in an improved embodiment, instead of applying directly the heartbeat instants found on the green PPG channel to the red and IR PPG channels, each value of $t_{b,r}[n]$ and $t_{b,ir}[n]$ is determined, respectively on the red PPG channel and on the IR PPG channel, by searching the local maximum of the PPG signal closest to the corresponding value of $t_{b,g}[n]$.

Figure 6:
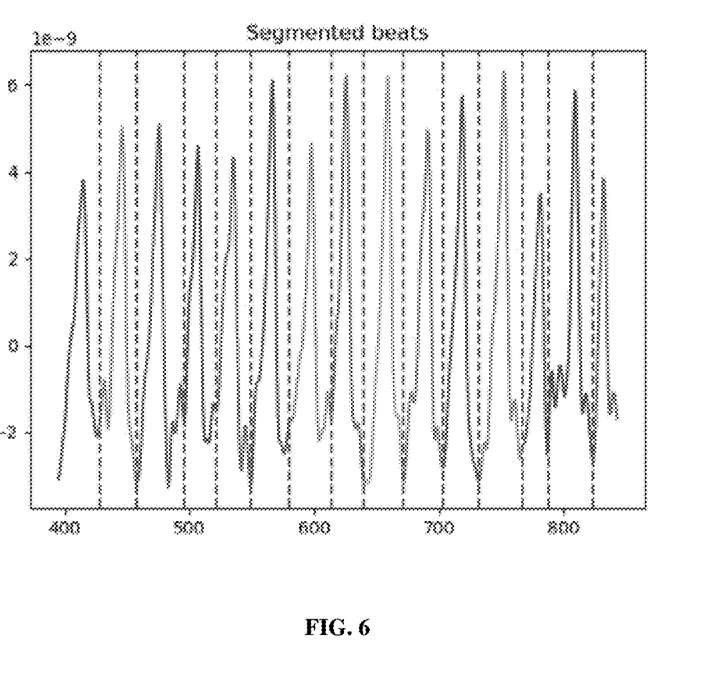
FIG. 6 is a graph showing the segmentation into successive patterns of a PPG signal corresponding to the IR channel of the wrist-worn monitoring device of FIG. 1.

An example of the resulting signal segmented into single heartbeat obtained, e.g., for the AC component of the red PPG signal of the pulse oximeter, is shown in FIG. 6.

The ratio of ratios RR is defined by:

$$RR = \frac{\left(\frac{AC}{DC}\right)_r}{\left(\frac{AC}{DC}\right)_{ir}}$$

where AC is the peak-to-peak amplitude of the PPG pulse and DC is the baseline of the PPG pulse.

In practice, the AC value is measured on each channel by computing the standard variation of the signal on each heartbeat signal segment or by computing the peak-to-peak amplitude of the signal on each heartbeat signal segment. The DC value is measured by computing the average signal level on each heartbeat signal segment.

Then, the ratio of ratios RR is determined for each heartbeat signal segment by computing one of the following values:

$$RR[n] = \frac{std(x_r^{AC}[n,:])}{mean(x_r^{DC}[n,:])} \times \frac{mean(x_{ir}^{DC}[n,:])}{std(x_{ir}^{AC}[n,:])}$$

$$RR[n] = \frac{max(x_r^{AC}[n,:]) - min(x_r^{AC}[n,:])}{mean(x_r^{DC}[n,:])} \times \frac{mean(x_{ir}^{DC}[n,:])}{max(x_{ir}^{AC}[n,:]) - min(x_{ir}^{AC}[n,:])}$$

The outputs are the vector RR as well as the instant associated to each computed RR, depicted as $t_{RR}$.

Motion estimation is performed by measuring the $L^2$ norm of the gyroscope sensor of the inertial motion unit 3, as follows:

$$gyro_{mag} = \sqrt{gyro_x^2 + gyro_y^2 + gyro_z^2}$$

In the following, $G_m$ is the vector containing the subsequent values of the gyroscope magnitude.

The signal quality is assessed by taking the motion estimation into account. More specifically, the signal quality assessment block in FIG. 4 outputs a signal sq at a rate of one value every 2 s. sq[n]=0 if the average value of $G_m$ on the preceding 2 s value is higher than a predefined threshold $\Gamma_{max}$ and sq[n]=1 if not.

Regarding the value of the predefined threshold $\Gamma_{max}$, it is set in accordance with the gyroscope average noise. By denoting $\sigma_{w,gyr}^2$ the power of this noise, $\Gamma_{max}$ can be defined as:

$$\Gamma_{max} = \alpha \sigma_{w,gyr}^2.$$

The exact value of $\alpha$ is set by measuring the norm of the gyroscope signal on signals corresponding to movement-free periods, in which the gyroscope signal is only composed of noise and imperceptible signals caused by natural body movements such as respiration.

The proposed algorithm relies on the analysis of the green channel of the PPG signal to measure the heart rate, as it is on this channel that the heart rate signal is the most visible.

First, the incoming green PPG signal is split into sliding windows of length $T_{w,HR}$ separated by steps of length $\Delta T_{HR}$. In one example, the length $T_{w,HR}$ is comprised in the range between 6 s and 10 s while the length of the steps $\Delta T_{HR}$ is comprises in between 0.5 s and 3 s.

Then, on each of these windows, a detrend operation may be performed to remove the average values as well as low-frequency trends.

Then, a Butterworth or Chebyschev band-pass filtering between 0.5 and 4 Hz is performed in order to isolate frequencies corresponding to the possible values of the heart rate.

The obtained signal is fed to a FFT processing stage which computes a FFT on $N_{FFT,HR}$ points which yields a frequency representation of the signal. In one example, number of points $N_{FFT,HR}$ is taken equal to $2^p$ with p between 8 and 12. If, for example, p=10, the number of points $N_{FFT,HR}$ is equal to 1024, and the frequential resolution will be equal to 1.46 bpm.

Finally, the main peak of this frequency representation is searched, and is returned as the estimated HR on the window.

In order to avoid erroneous estimations which may be caused by transitory glitches creating parasite peaks on the frequency representation of the PPG signal, the $N_{med,HR}$ latest estimates are stored in a buffer, and the median value of this buffer is returned as the final heart rate estimate. The $N_{med,HR}$ value may range between 5 and 15.

By way of example, the following set of parameters can be selected:

$T_{w,HR}=8$ s $\Delta T_{HR}=2$ s $N_{FFT,HR}=1024$, which gives a frequential resolution of 1.46 bpm $N_{med,HR}=11$.

Figure 4:
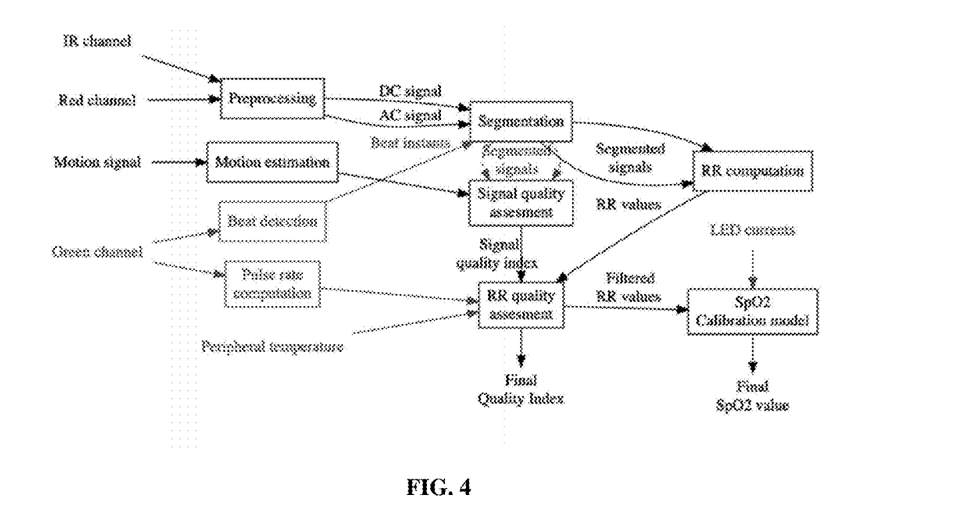
FIG. 4 is a block diagram showing steps of a method according to the invention for determining the blood oxygen saturation (SpO2) of a subject, e.g. by means of the wrist-worn monitoring device of FIG. 1.

Thus, the pulse rate computation block in FIG. 4 outputs a value of HR every two seconds in the vector HR.

The purpose of the RR quality assessment block is, based on the sequence of ratios-of-ratios computed on each heartbeat signal segment and the output of the signal quality assessment block, to provide both:

filtered RR values at a constant rate (for example the constant rate of one every 2 s, RR_f), a final quality index reflecting the quality of the estimation, q.

To do so, the RR quality assessment block implements the following algorithm.

In a first step, to lower the noise level, the RR values are filtered using the following strategy:

first, all RR values that are deemed too low or too high and thus not corresponding to a credible SpO2 value are removed; in practice the removal thresholds are computed according to the function $f$ which yields SpO2 values from RR values by removing RR values which would correspond to an incorrectly high (for example higher than 100%) or low (for example lower than 60%) SpO2 value.

then, in order to filter the remaining RR values, the latest computed values are stored in a buffer which keeps all values measured in a predefined period of time (for example in the range between 10 and 30 seconds);

the final value of RR used to measure the SpO2 value, called $RR_n$, is obtained by computing the median value of the stored RR values, which is equivalent to applying a rolling median filter on the RR values.

In one example, the RR values lower than 0.2 or higher than 1.3 are removed as not corresponding to a credible SpO2 value.

Then, to measure the quality of estimation of $RR_n$, measurements are performed to determine how the RR values stored in the buffer used to compute the median are scattered. In other words, the measurement of the variance of this buffer is used to estimate how reliable the value of $RR_n$ is. This information is useful for two purposes.

First, it is used to define $\alpha_n$, the update factor to be applied to the value of $RR_n$ such that the final estimated value of RR is defined as:

$$\overline{RR_n} = \alpha_n RR_n + (1-\alpha_n)\overline{RR_{n-1}}, \quad \alpha_n = \frac{1}{1+\frac{\text{var}(rr)}{\tilde{\sigma}_{rr}^2}}$$

where var(rr) is the variance of the RR values stored in the buffer and $\tilde{\sigma}_{rr}^2$ is a scaling parameter controlling how quality is affected by the variance of RR values. In a typical example, $\tilde{\sigma}_{rr}^2=0.01$.

Furthermore, it is used to compute a quality index QI associated with the estimation of $RR_n$ by computing the following n-th value of the QI:

$QI_n=(A*\alpha_n+1)\beta_n$ where A is a multiplicative factor (for example equal to 1000), $\beta_n$ is the ratio between the number of RR values stored in the RR buffer, which corresponds to the number of acceptable detected heartbeats in the buffer, and the number of heartbeats predicted according to the value of heart rate computed with the algorithm detailed above for the pulse rate computation block.

According to one embodiment, the quality index QI is the product of at least two of three terms $\alpha$, $\beta$, $\gamma$ such that:

$\alpha$ measures the dispersion of the RR measurements: the further they are apart, the lower $\alpha$ is, so as to reflect the fact that the algorithm is unable to converge to a stable RR value;

$\beta$ measures the consistency between the number of heartbeats on which the measure of RR is performed and the number of heartbeats which should have been obtained based on the estimated heart rate: this is to counterbalance wrongly high values of $\alpha$ that can be obtained in some cases in which very few RR values are considered;

$\gamma$ measures the influence of the skin temperature by comparing the measured skin temperature T to a reference temperature $T_{th}$ under which it can be difficult to measure RR values with accuracy because of poor perfusion, e.g. $\gamma=\exp(T-T_{th})$ with $T_{th}$ of the order of 34° C.

Figure 7:
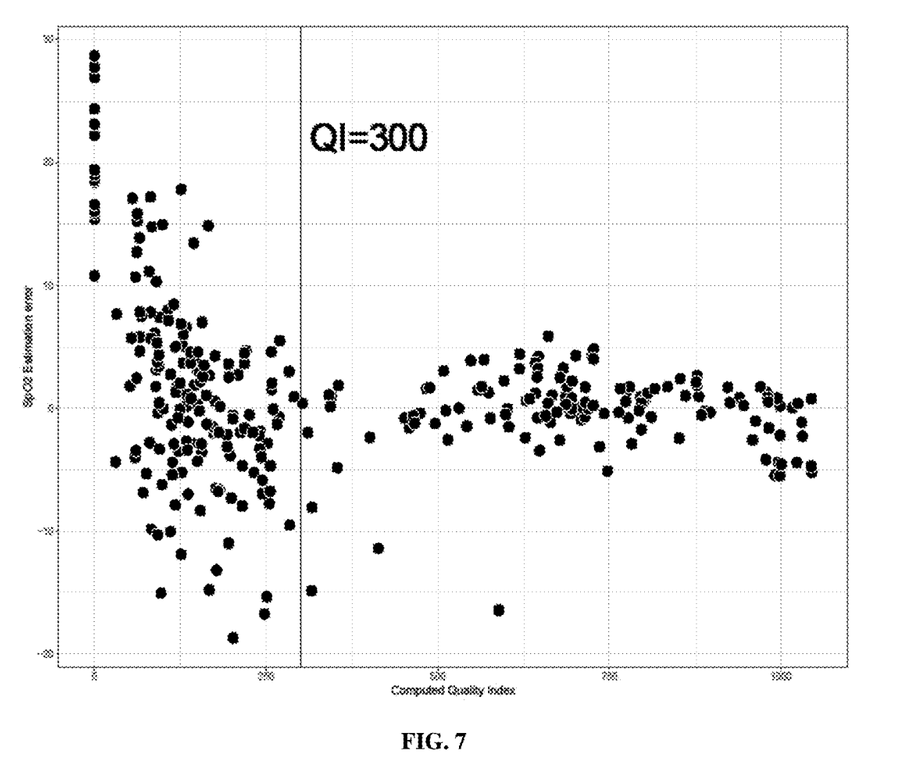
FIG. 7 is a graph showing the error associated with each signal segment comprising a heartbeat as a function of their associated quality index.

Finally, the value of QI is multiplied by the corresponding value of sq computed by the signal quality assessment block so that the final quality index q equals 0 if motion has been detected and QI if not. FIG. 7 shows good correlation of the quality index q with the error estimation of each signal segment associated to one heartbeat.

Finally, the SpO2 value is obtained by applying a calibration model to the measured value of $\overline{RR_n}$. In a first approach, an average theoretical model can be computed giving:

$\widehat{SpO2}_n = B - C^{\overline{RR_n}}$ where B and C are parameters of the model that may be optimized on the basis of a characterization of the photodetector design. This theoretical model cannot encompass all details of the photodetector design and is bound to yield under-optimal performance. Thus, it is advantageous to perform a calibration study to optimize the transfer function from RR to SpO2.

According to the invention, it is proceeded to a calibration of a linear model capturing the relationship between SpO2 and the LED currents of the red, infrared and green LEDs. LED currents are correlated to the phototype of the subject. In particular, the phototype will affect the ratio of DC values of the signal. Therefore, it is desirable to adjust the calibration model according to the phototype of the subject. In addition, LED currents affect the exact value of the wavelength emitted by each LED. In particular, it has been determined that the relationship of the centroid wavelength to the logarithm of the LED current can be approximated by a second order polynomial.

More precisely, the calibration model is a second order polynomial calibration model having as parameters:
  the RR value and its squared value $RR^2$,
  the logarithm of the LED current of at least one of the LEDs and its squared value.

The invention claimed is:

1. A computer-implemented method for evaluating quality of ratio of ratios, RR, values computed for at least three photoplethysmographic, PPG, signals corresponding to distinct wavelengths, wherein each PPG signal comprises successive heartbeat signal segments, said method comprising:
  segmenting a first PPG signal corresponding to a red wavelength and a second PPG signal corresponding to an infrared wavelength into a plurality of signal segments each corresponding to one heartbeat, by:
    extracting a sequence of heartbeat instants $t_{b,g}[n]$ from a third PPG signal corresponding to a third wavelength;
    segmenting the first and second PPG signals into a plurality of signal segments, each signal segment corresponding to one heartbeat, using the sequence of heartbeat instants $t_{b,g}[n]$ extracted from the third PPG signal,
  for each given signal segment, computing a sequence of RR values, and
  evaluating, for each given signal segment, a quality index of the sequence of computed RR values on the basis of a computed heart rate and/or a measured peripheral temperature corresponding to the given signal segment.

2. The method according to claim 1, wherein the quality index of a sequence of computed RR values involves a term resulting from a comparison between the number of heartbeats in the period of time on which the computed RR values are determined and the number of heartbeats calculated from the computed heart rate for said period of time.

3. The method according to claim 2, wherein the quality index of a sequence of computed RR values is a product of at least two among the terms resulting from the dispersion calculation, the heartbeat comparison and the temperature comparison.

4. The method according to claim 1, wherein the computed heart rate is obtained by identifying a maximum peak in the frequency domain in a third PPG signal corresponding to a third wavelength.

5. The method according to claim 1, wherein the sequence of heartbeat instants $t_{b,g}[n]$ is applied to the first and second PPG signals such that:

$$\forall n, t_{b,r}[n] = t_{b,ir}[n] = t_{b,g}[n],$$

each heartbeat signal segment of the first PPG signal and the second PPG signal being defined according to the following expressions:

$$x_r[n,:] = ppg\_r[\tfrac{1}{2}(t_{b,g}[n] + t_{b,g}[n+1]) : \tfrac{1}{2}(t_{b,g}[n+1] + t_{b,g}[n+2])],$$

$$x_{ir}[n,:] = ppg\_ir[\tfrac{1}{2}(t_{b,g}[n] + t_{b,g}[n+1]) : \tfrac{1}{2}(t_{b,g}[n+1] + t_{b,g}[n+2])].$$

6. The method according to claim 5, wherein each heartbeat instant $t_{b,r}[n]$ and $t_{b,ir}[n]$ is determined, respectively for the first and second PPG signals, by searching the local maximum of the PPG signal closest to the corresponding value of $t_{b,g}[n]$.

7. The method according to claim 1, wherein the quality index of a sequence of computed RR values involves a term resulting from a comparison between a measured peripheral temperature and a reference temperature.

8. The method according to claim 1, wherein the quality index of a sequence of computed RR values involves a term resulting from the calculation of a dispersion of the computed RR values for the different signal segments.

9. The method according to claim 1, further comprising:
  for each given signal segment, estimating the fitness of the given signal segment for RR estimation and outputting a signal quality index for the given signal segment,
  for each given signal segment, evaluating the quality of the computed RR value on the basis of the signal quality index for the given signal segment.

10. A method for evaluating an SpO2 value based on a ratio of ratios, RR, value evaluated according to the method of any one of the preceding claims, wherein the photoplethysmographic, PPG, signals are obtained by using LEDs as light sources, the SpO2 value being obtained using a calibration model having as parameters the RR value and the LED current of at least one of the LEDs.

11. The method according to claim 10, wherein the calibration model is a second order polynomial calibration model having as parameters:
  the RR value and its squared value $RR^2$,
  the logarithm of the LED current of at least one of the LEDs and its squared value.

12. A non-transitory computer readable medium comprising instructions for the implementation of the steps of a method according to claim 1 when the instructions are executed by a computer.

13. A system for evaluating the quality of ratio of ratios, RR, values computed for at least three photoplethysmographic, PPG, signals corresponding to distinct wavelengths, wherein each PPG signal comprises successive heartbeat, said system comprising:
  a segmentation module for segmenting a first PPG signal corresponding to a red wavelength and a second PPG signal corresponding to an infrared wavelength into a plurality of signal segments each corresponding to one heartbeat pattern,
  a computation module for computing, for each given signal segment, a sequence of RR values, by:
    extracting a sequence of heartbeat instants $t_{b,g}[n]$ from a third PPG signal corresponding to a third wavelength;
    segmenting the first and second PPG signals into a plurality of signal segments using the heartbeat patterns extracted from the third PPG signal, and
  an evaluation module for evaluating, for each given signal segment, a quality index of the sequence of computed RR values on the basis of a computed heart rate and/or a measured peripheral temperature corresponding to the given signal segment.

14. A system for performing a pulse oximetry comprising:
  at least two light sources configured to emit light at two distinct wavelengths,
  an acquisition module configured to acquire the photoplethysmographic, PPG, signals resulting from the illumination of tissues of a subject by means of said light sources, a system according to claim 13 for evaluating the quality of ratio of ratios values computed for the PPG signals corresponding to the two distinct wavelengths.

* * * * *